United States Patent
Thomas, II

[19]

[11] Patent Number: 5,810,738
[45] Date of Patent: Sep. 22, 1998

[54] MINIATURIZED BLOOD PRESSURE MONITOR KIT

[76] Inventor: Donald Dee Thomas, II, 382 Potter Rd., Aptos, Calif. 95003

[21] Appl. No.: 699,819

[22] Filed: Aug. 19, 1996

Related U.S. Application Data

[63] Continuation of Ser. No. 289,778, Aug. 12, 1994, abandoned.

[51] Int. Cl.⁶ .................................................. A61B 5/02
[52] U.S. Cl. .......................... 600/505; 600/486; 600/488; 600/493; 600/561
[58] Field of Search ..................... 128/672, 673, 128/675, 677, 680, 687, 692, 748

[56] References Cited

U.S. PATENT DOCUMENTS

| | | | |
|---|---|---|---|
| 4,217,910 | 8/1980 | Khalil | 128/692 |
| 4,347,851 | 9/1982 | Jundanian | 128/668 |
| 4,523,679 | 6/1985 | Paikoff et al. | 206/438 |
| 4,576,180 | 3/1986 | Taheri | 128/673 |
| 4,611,601 | 9/1986 | Bowman | 128/673 |
| 4,621,646 | 11/1986 | Bryant | 128/692 |
| 4,638,811 | 1/1987 | Bisera et al. | 128/673 |
| 4,712,566 | 12/1987 | Hok | 128/743 |
| 4,867,170 | 9/1989 | Takahashi | 128/690 |
| 4,924,872 | 5/1990 | Frank | 128/673 |
| 4,928,830 | 5/1990 | Brewer | 206/438 |
| 5,002,061 | 3/1991 | Close et al. | 128/687 X |
| 5,048,537 | 9/1991 | Messinger | 128/673 |
| 5,105,818 | 4/1992 | Christian et al. | 128/691 |
| 5,284,138 | 2/1994 | Kujawski | 128/634 |

*Primary Examiner*—Robert L. Nasser
*Assistant Examiner*—Ryan Carter
*Attorney, Agent, or Firm*—Young & Basile, P.C.

[57] ABSTRACT

A blood pressure monitor kit suitable for use in emergency scenarios such as cardiopulmonary arrest situations. The kit includes a catheter for insertion in the femoral artery of the patient, a transducer arranged to receive blood pressure signals from the catheter and operative to convert the blood pressure signals into electric signals; a housing; a monitor mounted in the housing and including electric circuitry arranged to receive the electric signals from the transducer and operative to generate at least one display indicative of a condition of the patient's blood pressure; a battery positioned within the housing and operative to power the electric circuitry; a switch associated with the housing for connecting the battery into the electrical circuitry to power the circuitry; and a securement device on the housing operative to secure the housing to a patient's body at a location proximate the location of the catheter insertion. The entire kit is packaged in a container which totally envelops the catheter, transducer, and monitor and forms a sealed, sterile package which may be opened upon demand. The kit is intended for one time use and is suitably disposed of after the single use.

16 Claims, 3 Drawing Sheets

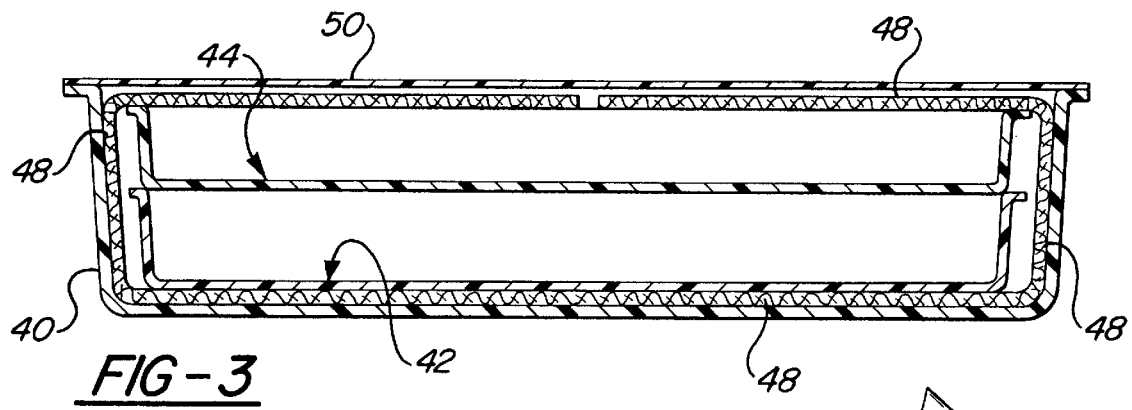
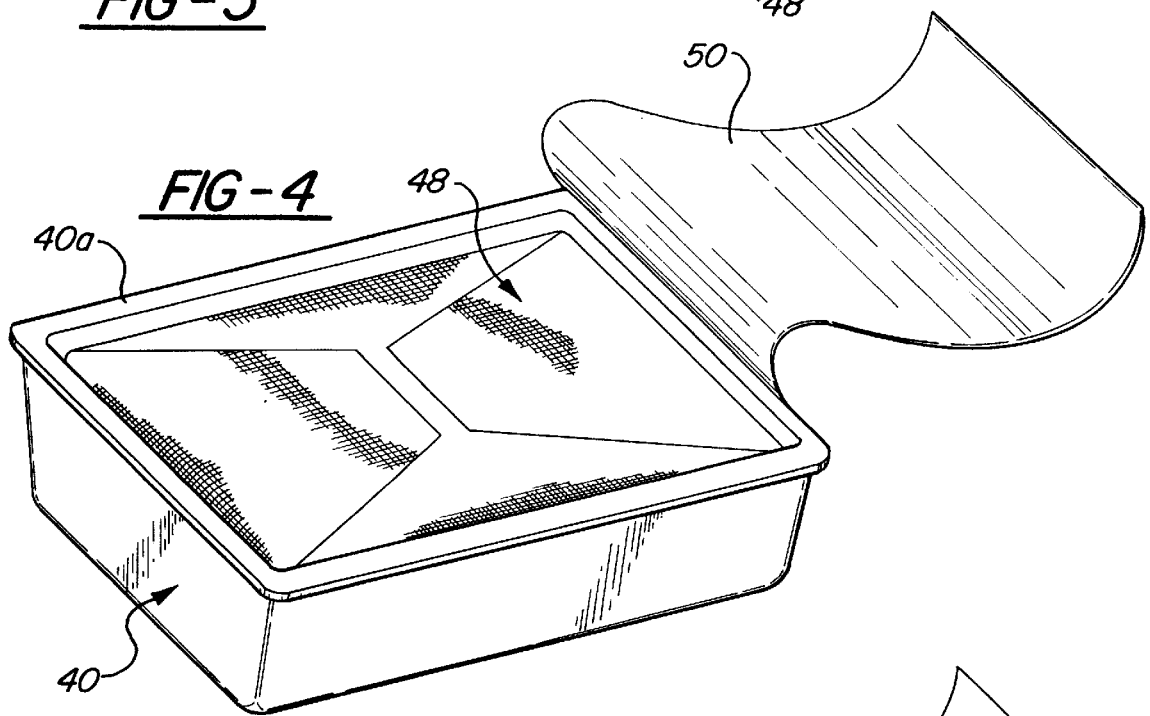
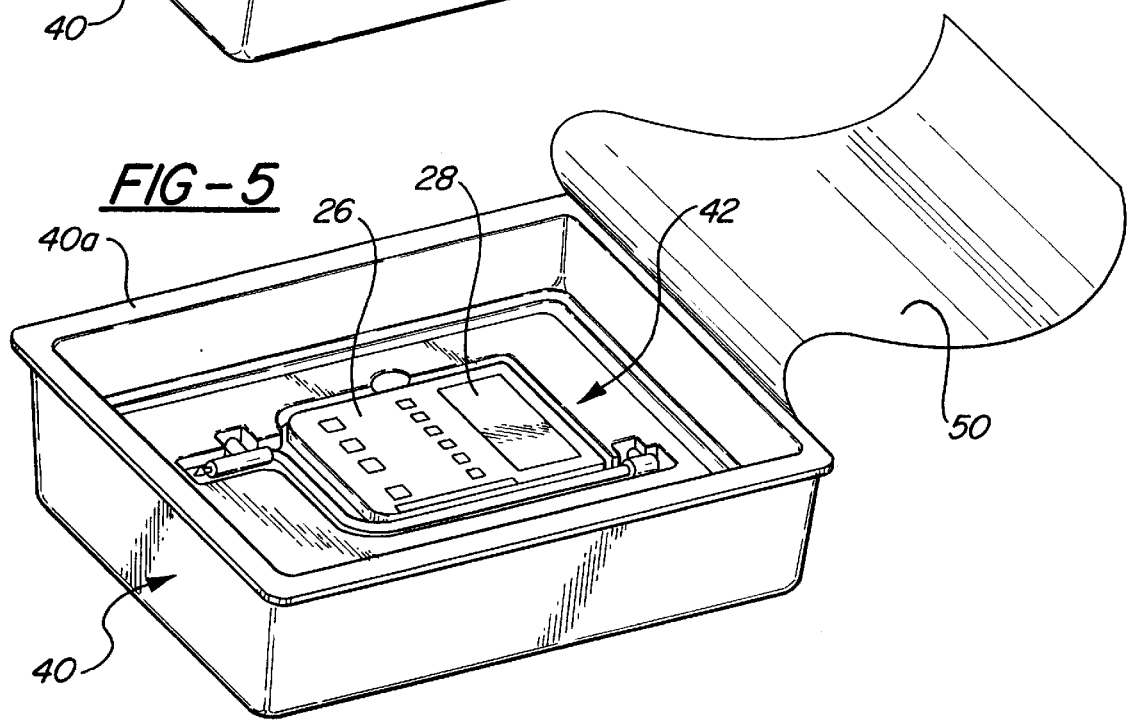

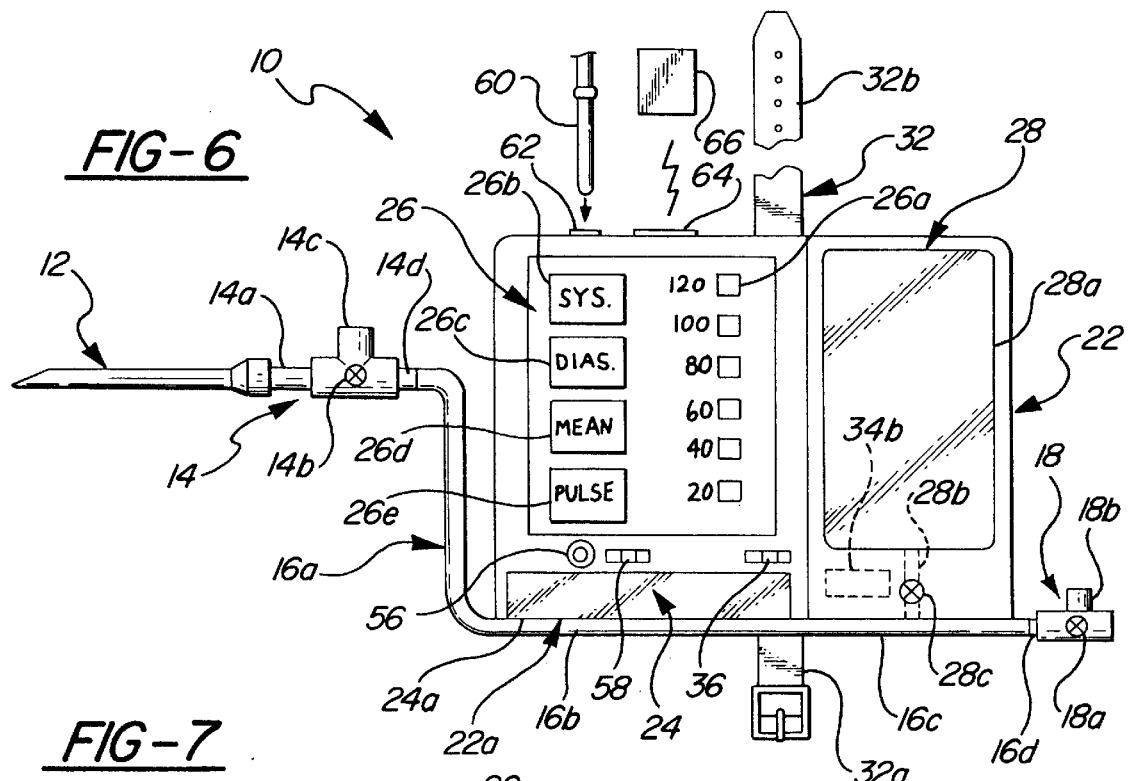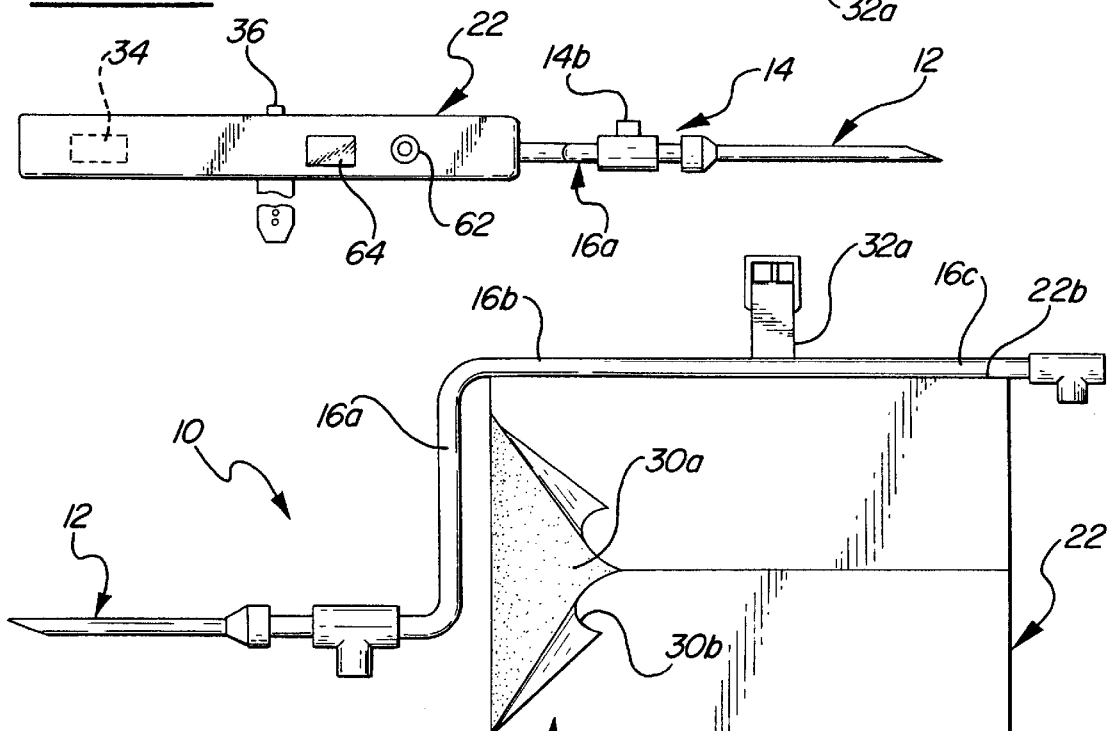

MINIATURIZED BLOOD PRESSURE MONITOR KIT

This is a continuation of application Ser. No. 08/289,778 filed on Aug. 12, 1994 now abandoned.

BACKGROUND OF THE INVENTION

This invention relates to blood pressure monitor devices and more particularly to a blood pressure monitor device particularly suitable for use in emergency environments.

There are currently 450–500,000 sudden deaths per year in the U.S. with 250,000 patients receiving cardiopulmonary resuscitation (CPR) by trained medical personnel. In order to optimize CPR procedures it is essential that an accurate blood pressure reading be provided during the procedure. Current blood pressure monitoring techniques during CPR are crude at best and include finger palpation and the use of a sphygmomanometer (blood pressure cuff). Only a very small fraction of patients undergoing CPR receive true arterial blood pressure monitoring. Achieving near physiologic arterial blood pressure is critical during cardiopulmonary resuscitation. Without arterial pressure monitoring there is no way to determine if CPR is effective. Currently, arterial blood pressure monitoring requires an indwelling catheter, a pressure transducer, and monitoring equipment that typically only exist in an intensive care type unit. Obtaining effective arterial blood pressure through monitoring during CPR has been shown to be essential in animal studies for satisfactory outcome. Human studies center on the quality of CPR as measured by blood pressure in the laboratory setting and also correlate improvement in outcome with improvement in blood pressure during CPR. In the sudden death patient group alone, improvement in the survival rate from 10 to 20% would result in at least 25,000 lives saved each year.

SUMMARY OF THE INVENTION

The primary object of the present invention is to provide a blood pressure monitor kit suitable for use during CPR and other emergency situations.

The blood pressure monitor kit of the invention includes a catheter adapted to be inserted into the artery of a patient; a transducer arranged to receive blood pressure signals from the catheter and operative to convert the blood pressure signals into electrical signals; a miniaturized monitor mounted in a housing and including electrical circuitry arranged to receive the electrical signals from the transducer and operative to generate at least one display indicative of a condition of the patient's blood pressure; a battery positioned within the housing and operative to power the electrical circuitry; and a switch associated with the housing for connecting the battery into the electrical circuitry to power the circuitry. This arrangement allows the kit to be provided as standard, required equipment on all code cards in all hospital emergency rooms and ambulances since the kit provides a sterile, portable, and disposable mechanism for monitoring blood pressure.

According to a further feature of invention, the kit further includes securement means on the housing operative to secure the housing to a patient's body at a location proximate the location of the catheter insertion. This arrangement further facilitates the convenience of the kit by allowing the main body of the kit to be attached directly to the patient's body rather than requiring a separate support apparatus.

According to a further feature of the invention, the kit further includes a container totally enveloping the catheter, transducer, and monitor and forming a sealed sterile package. This arrangement allows the container to be opened upon demand to provide a disposable, sterile blood pressure monitor.

According to a further feature of the invention, the kit further includes a conduit for conducting blood from the catheter to the monitor and means for flushing the conduit. The flushing means may comprise a syringe in communication with the conduit and operative when actuated to deliver a flushing solution to the conduit, or may comprise a pressurized reservoir mounted on the housing and containing a flushing solution which is continuously fed to the conduit.

According to a further feature of the invention a stop cock is positioned in the conduit between the catheter and the housing. Using this stop cock arrangement, arterial blood gases can be readily sampled for analysis.

In the disclosed embodiment of the invention, the kit further includes a tray positioned removably within the container; the kit includes a plurality of catheters of varying sizes and configurations and all the catheters are positioned in the tray so as to provide a selection of catheters for use with the monitor; the container defines a lower level below the tray; and the transducer and monitor are positioned in the lower level of the container beneath the tray. This specific packaging allows the kit to be provided in a compact, sterile, readily-usable form.

According to the invention methodology, the kit is moved to a location proximate an artery of the patient and the catheter of the kit is inserted into the patient's artery. This methodology, which capitalizes on the lightweight and small size of the invention kit, allows accurate blood pressure monitoring to be provided in virtually all emergency scenarios.

According to a further feature of the invention methodology, the housing mounting the monitoring device is secured to the patient's body at a location proximate the location of the catheter insertion. This methodology, which again capitalizes on the lightweight and small size of the invention kit, allows the secure positioning of the monitoring device on the patient's body adjacent the insertion location.

BRIEF DESCRIPTION OF THE DRAWING

FIG. 3 is a cross-sectional view of the kit taken on line 3—3 of FIG. 2;

FIG. 4 is a view of the kit with a sterile cover peeled back;

FIG. 5 is a view of the kit with an upper tray removed;

FIG. 6 is a top view of the operative elements of the kit removed from the container;

FIG. 7 is a side view of the operative elements of the kit removed from the container; and FIG. 8 is a bottom view of the operative elements of the kit removed from the container.

DETAILED DESCRIPTION OF THE PREFERRED EMBODIMENT

Figure 1:
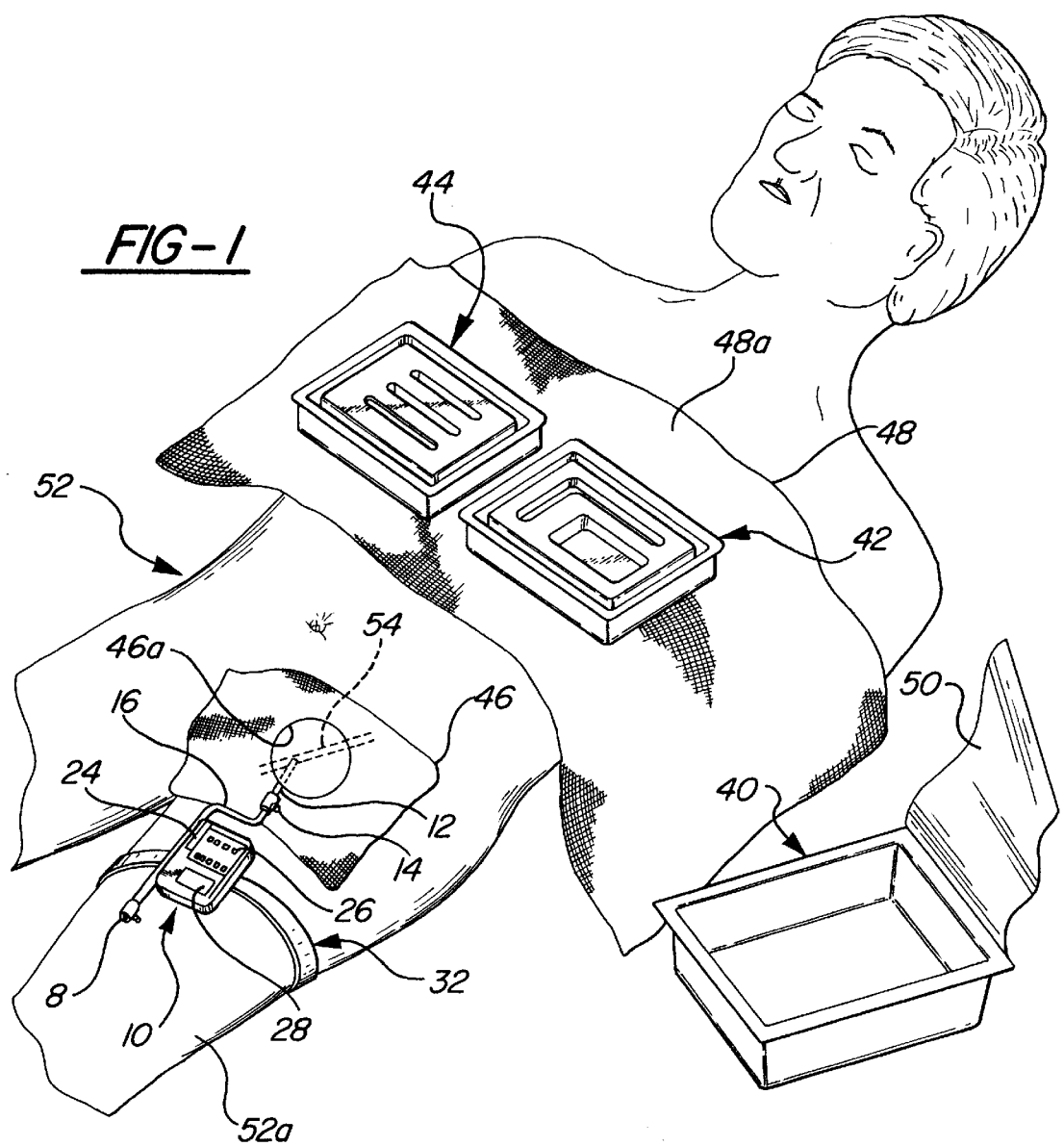
FIG. 1 is a perspective view showing the invention blood pressure monitor kit in use to monitor the blood pressure of a patient in an emergency situation.
Figure 2:
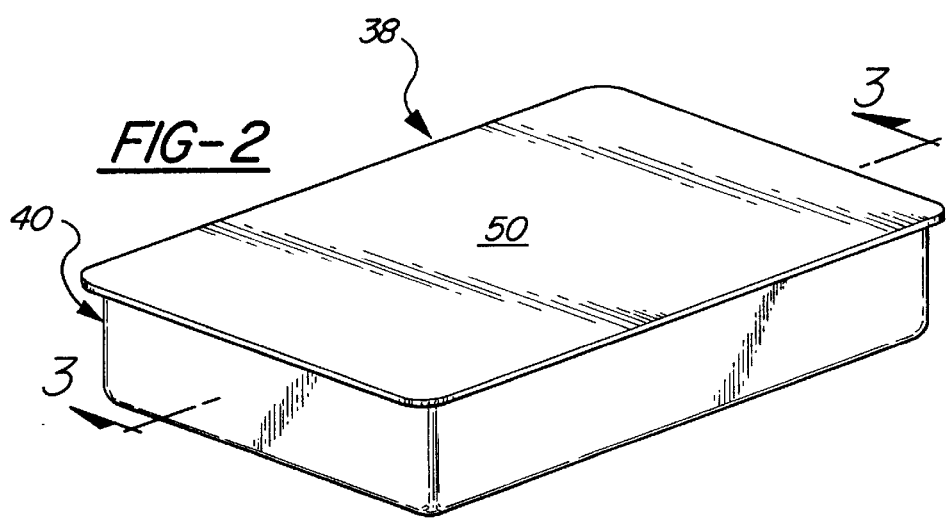
FIG. 2 is a perspective view of the blood pressure monitor kit.

The invention blood pressure monitor kit in the form in which it is supplied to emergency rooms, ambulances, and other emergency scenarios is seen in FIG. 2, and the kit as it is utilized in a typical emergency scenario is seen in FIG. 1.

The operative elements of the kit constitute a blood pressure monitor 10. Monitor 10 includes a catheter 12, a first stop cock 14, a conduit 16, a second stop cock 18, and a housing assembly 20.

Catheter 12 includes an operative end 12a for insertion in an artery of a patient undergoing trauma and a connector end 12b.

Stop cock 14 is connected at one end 14a by a LUER connection to the connector end 12b of the catheter and includes a valve 14b and an orthogonal branch 14c.

Conduit 16 is formed of a suitable flexible plastic material and includes a connector portion 16a connected to the other end 14d of the stop cock, an operative portion 16b, and a flushing portion 16c.

Stop cock 18 is secured to the free end 16d of the flushing portion 16c of the conduit and includes a valve 18a and an orthogonal branch 18b.

Housing assembly 20 includes a housing 22, a transducer 24, a monitoring device 26, a reservoir 28, and housing attachment means 30,32.

Housing 22 has a generally rectangular configuration, may be formed of a suitable molded plastic material, and is operatively associated with and secured to conduit portions 16b and 16c along one edge 22a of the housing.

Transducer 24 is mounted in the housing 22 with one edge 24a of the transducer in operative association with the operative portion 16b of conduit 16 so that the transducer may operate, in known manner, to receive blood pressure signals from the catheter 12, as delivered to the operative portion 16b of the conduit, and convert the blood pressure signals into analog electric signals having a waveform corresponding to the waveform of the rising and falling blood pressure of the patient.

Monitoring device 26 is mounted in housing 22 immediately above transducer 24 and includes an analog/digital convertor arranged to receive the analog signals from the transducer for conversion to digital signals and further electric circuitry operative to generate at least one display indicative of a condition of the patient's blood pressure. In the embodiment illustrated, the displays include a plurality of vertically stacked windows 26a for displaying successively higher blood pressure readings, a systolic blood pressure window 26b, a diasystolic blood pressure window 26c, a mean blood pressure window 26d and a heart rate or pulse window 26e. Displays 26a–26e may comprise Light Emitting Diode (LED) displays or liquid crystal displays in known manner.

Reservoir 28 is mounted in housing 22 along side of monitoring device 26 and comprises a heparinized saline pressurized reservoir 28a connected to the flushing portion 16c of conduit 16 via a flushing conduit 28b. Reservoir 28a comprises a pressurized plastic bag containing the pressurized saline solution and the flow of the saline solution out of the bag 28a into conduit portion 16c is controlled by a valve 28c.

Attachment means 30 comprises a sticky surface 30a provided on the bottom 22a of the housing and paper segments 30b. Segments 30b normally cover the sticky surface 30a and may be removed in known manner to provide a self-adhering surface to facilitate attachment of the housing to the patient.

Attachment means 32, which may be provided in addition to attachment means 30 or as an alternative to attachment means 30, comprises a strap having coacting attachment portions 32a, 32b secured to opposite side edges 22b, 22c of the housing and operative in known manner to strap the housing to a limb of a patient.

Housing assembly 20 further includes a battery 34 positioned in a suitable compartment provided within the housing and a switch 36 provided on the housing and operative when moved from an OFF to an ON position to place the battery in electrical communication with the electrical circuitry of the monitor so as to power the monitor. Since the power requirements of the monitor are very low, battery 34 may comprise, for example, a miniature watch battery.

The invention blood pressure monitor kit further includes a container assembly 38 for housing the monitor 10. Container assembly 38 includes a container 40, a lower tray 42 sized to fit in the lower region of the container, and an upper tray 44 sized to fit in an upper region of the container in overlying relation to lower tray 42.

Container 40 and trays 42 and 44 are formed of a suitable molded plastic material, have a rectangular configuration, and are arranged so that the trays may be positioned within the interior of container 40 in nesting relation.

Lower container 42 is provided in known manner with suitable grooves and indentations in its upper face to nestingly receive the monitor 10 with the exception of catheter 12. Specifically, as best seen in FIG. 5, the upper face of tray 42 receives stop cock 14, conduit 16, transducer 24, monitor 26, reservoir 28, and stop cock 18 in suitable indentations in the upper face of the tray so that, once the upper tray 44 has been removed from container 40, monitor 10 (excluding catheter 12) may be readily removed from the tray 42. Alternatively, tray 42 may be removed from container 40 whereafter monitor 10 may be removed from the tray.

Upper tray 44 includes a plurality of suitable grooves and indentations to receive one or more catheters 12 as well as accessory equipment such as a scalpel, guide wires, syringes, needles, Lidocaine, antiseptic skin preparation solution, sutures, bandages, and a small drape 46.

Upper and lower trays 42 and 44 are wrapped in a sterile manner in a large drape 48 which extends completely around the stacked trays in the container assembly 38. Container 40 is sealed in a sterile manner by a plasticized paper cover 50 which is normally securely bonded to the upper rim 40a of container 40 but which can be readily peeled back, as seen in FIGS. 4 and 5, to expose the contents of trays 42 and 44.

A typical application of the invention blood pressure monitor kit is seen in FIG. 1 wherein a patient 52 is undergoing CPR in an emergency setting such as in an ambulance or in an emergency room. As previously noted, it is extremely important to provide an accurate and ongoing indication of the patient's blood pressure during the CPR procedure so as to judge the effectiveness of the CPR.

In the use of the invention blood pressure monitor kit to provide an accurate and ongoing indication of the patient's blood pressure during an emergency CPR procedure, the kit is moved to a location proximate the femoral artery 54 of the patient; cover 50 is peeled back to expose the contents of container 38; trays 42 and 44 are removed from the container; large drape 48 is laid out at a convenient location proximate the patient (for example, as illustrated, over the mid-section of the patient) to provide a sterile field 48a; trays 42 and 44 are positioned on sterile field 48a; monitor 10 (less catheter 12) is removed from lower tray 42; a suitable catheter 12 is selected by the attending medical person from the array of catheters provided in upper tray 44 with the particular catheter chosen depending upon professional preference and arterial size; small drape 46 is positioned over the groin of the patient with a central aperture 46a of the drape exposing the groin area and thereby allowing access to femoral artery 54; the chosen catheter 12 is inserted into femoral artery 54 utilizing the Seldinger technique (wherein a needle is placed in the artery, a wire is inserted through the needle, the needle is removed, the catheter and a corresponding dilator are placed over the wire, and the wire and dilator are removed); the selected catheter 12 is connected by a LUER connection to stop cock 14; housing 22 is secured to the patient's thigh 52a at a location proximate the location of the catheter insertion utilizing either the sticky self-adhering surface 30a on the bottom of the housing and/or the strap 32 positioned around the leg of the patient; the system is flushed with a saline or heparinized saline solution; switch 36 is moved to an ON position to power the monitor; and the catheter is sewn in position. The attending medical person is thereafter provided with an ongoing and accurate indication of the blood pressure of the patient so as to provide an ongoing indication of the effectiveness of the CPR or other procedure being administered to the patient.

Specifically, once the blood pressure monitor is in place, the attending medical person is provided with a continuous averaged measure of the systolic, diastolic and mean blood pressure of the patient, as well as a continuous indication of the pulse of the patient. The rising and falling blood pressure is also presented in graphic form in the series of windows 26a with windows 26a successively lighting with each beat of the patient's heart to indicate the blood pressure attained during that specific beat. During this procedure, valve 28c is open to allow a continuous drain of a flush solution (for example, heparinized saline) from reservoir 28a into conduit portion 16c so as to ensure that the conduit will not clot during use. The conduit 16 may also be flushed during use by a syringe applied to stop cock 18 and arterial blood gases may be drawn at any time during the procedure utilizing branch 14c of stop cock 14 in coaction with valve 14b.

Although the invention blood pressure monitor kit has been illustrated as being employed in association with the femoral artery, it will be apparent that the kit may also be employed with other arteries such as the radial artery.

Monitoring device 26 preferably includes a microprocessor chip and the chip preferably includes memory so that the blood pressure and pulse information provided during a given CPR procedure may be retrieved for downloading into a computer for subsequent analysis. The retrieval may be accomplished by a plug 60 inserted into a jack 62 in housing 22 or by an infrared transmitter 64 provided on housing 22 and coacting with an infrared receiver 66. In addition to retrieving the stored information relating to a particular procedure after the procedure has been completed, the monitor may also be equipped to transmit a continuing stream of blood pressure and pulse information, as it is being received during a particular procedure, to a remote receiving location, such as a hospital to which the patient is being transported as the procedure is being performed. Monitoring device 26 also preferably includes an alarm to indicate that the patient's blood pressure and/or pulse has gone out of a predetermined range with lower and upper limits. For example, an LED 56 may be provided in housing 22 controlled by a switch 58 so that, when the switch is moved to an ON position, LED 56 will be energized whenever the patient's pulse and/or blood pressure goes above or below the predetermined range to serve as an alarm to the attending medical person. Alternatively, an audible signal may be provided when the pulse and/or blood pressure goes above or below the predetermined range.

Once the need for monitoring has ended, the entire blood pressure monitor kit may be suitably disposed of since the kit is intended for one time use and is not intended for resterilization.

The invention blood pressure monitor kit will be seen to provide many important advantages as compared to current techniques utilized to monitor blood pressure during emergency procedures. Specifically, as compared to the finger palpation employed in many emergency CPR scenarios, the invention kit provides an ongoing and accurate indication of the patient's blood pressure; as compared to the use of a sphygmomanometry device in situations where a blood pressure cuff is available, the invention kit provides a continuous ongoing indication of blood pressure as compared to the occasional readings provided by the blood pressure cuff; as compared to an intensive care unit setting in which permanently installed, expensive, bulky blood pressure monitoring equipment is available, the invention kit requires an investment that is only a tiny fraction of the investment required for the permanently installed blood pressure monitoring equipment and the invention kit, by virtue of its lightweight and small size, may be delivered to the patient in the emergency scenario, such as in an ambulance, and may be directly applied to the patient's body. For example, a monitoring device 26 constructed in accordance with the invention may have dimensions of 2½ by 5 by 1 inch and may have a weight of 125 grams. This extremely small size and extremely lightweight, as compared to the prior art permanent blood pressure monitoring devices, allows the invention blood pressure kit to be readily moved to a location proximate an artery of the patient for insertion of the catheter into the artery. The extremely small size and lightweight also allow the monitoring device to be readily and comfortably attached to the patient's body.

Whereas a preferred embodiment of the invention has been illustrated and described in detail, it will be apparent that various changes may be made in the disclosed embodiment without departing from the scope or spirit of the invention.

I claim:

1. A miniature blood pressure monitoring kit comprising:

a housing;

a catheter adapted to be inserted into a blood vessel of a patient;

a conduit formed of a tubular material and including a flexible connector portion in fluid communication with the catheter and an operative portion carried by the housing and in fluid communication with the connector portion;

a transducer carried by the housing and positioned in operative association with the operative portion of the conduit and operative to receive blood pressure signals from the operative portion of the conduit and convert the blood pressure signals into electrical signals;

a monitoring device mounted in the housing and including electric circuitry arranged to receive the electrical signals from the transducer and operative to generate at least one display indicative of a condition of the patient's blood pressure;

a battery positioned within the housing and operative to power the electric circuitry;

a switch associated with the housing for connecting the battery into the electric circuitry to power the circuitry;

securement means on the housing operative to secure the housing to a patient's body at a location proximate the location of the catheter insertion; and a reservoir containing a flushing solution and having an outlet for communication with the conduit to flush the conduit.

2. A monitor according to claim 1 wherein the kit further includes a container totally enveloping the catheter, transducer and monitoring device and forming a sealed, sterile package which may be opened upon demand to provide a disposable blood pressure monitor kit for emergency use applications.

3. A blood pressure monitor kit according to claim 1 wherein the conduit further includes a flushing portion communicating with the operative portion and the outlet of the reservoir communicates with the conduit flushing portion.

4. A monitor according to claim 3 wherein the kit further includes a container totally enveloping the catheter, transducer and monitoring device and forming a sealed, sterile package which may be opened upon demand to provide a disposable blood pressure monitor kit for emergency use applications.

5. A miniaturized blood pressure monitor kit according to claim 3 wherein the kit further includes a stopcock at a free end of the conduit flushing portion, the reservoir outlet communicating with the stopcock to flush the conduit.

6. A blood pressure kit according to claim 5 wherein the kit is totally enveloped in a container and the kit further includes a tray positioned removably within the container and containing the catheter.

7. A kit according to claim 6 wherein the kit includes a plurality of catheters of varying sizes and configurations and all of the catheters are positioned in the tray so as to provide a selection of catheters for use with the monitor.

8. A kit according to claim 5 wherein the kit further includes a further stopcock in the conduit between the catheter and the conduit operative portion.

9. A method of monitoring the blood pressure of a patient in an emergency situation comprising the steps of:

providing a disposable sterile blood pressure monitor kit including a housing; a catheter adapted to be inserted into a blood vessel of the patient; a conduit formed of a tubular material and having a flexible connector portion and an operative portion carried by the housing and communicating with the connector portion; a transducer carried by the housing, juxtaposed to the operative portion of the conduit, and operative to receive blood pressure signals from the operative portion of the conduit and convert the blood pressure signals into electrical signals; a battery positioned in the housing; a switch on the housing connected to the battery; a monitoring device positioned in the housing, powered by the battery, controlled by the switch, and including electric circuitry arranged to receive electrical signals from the transducer and operative to generate at least one display indicative of an aspect of the patient's blood pressure; securement means on the housing operative to secure the housing to a patient's body at a location proximate the location of the catheter insertion; and a reservoir containing a flushing solution and having an outlet for communication with the conduit;

moving the kit to a location proximate a blood vessel of the patient;

inserting the catheter into the blood vessel;

securing the housing to the patient's body at a location proximate the location of the catheter insertion; and flushing the conduit utilizing flushing solution delivered from the reservoir outlet to the conduit.

10. A method according to claim 9 wherein the blood vessel is the femoral artery and the housing is secured to the patient's thigh.

11. A method according to claim 10 wherein the housing is adapted to be secured to the patient's thigh utilizing said securement means in the form of a strap connected to the housing.

12. A method according to claim 9 wherein the housing is secured to the patient's thigh utilizing said securement means in the form of a self-adhering surface provided on the housing.

13. A miniaturized blood pressure monitor kit according to claim 7 wherein:

the container defines a lower level below the tray and the transducer and monitoring device are positioned in the lower level of the container beneath the tray.

14. A method according to claim 9 wherein the kit is provided as a sealed kit which is opened upon the occurrence of the emergency situation and disposed of after usage in association with the emergency situation.

15. A miniaturized blood pressure monitor kit comprising:

a catheter adapted to be inserted into a blood vessel of a patient;

a transducer arranged to receive blood pressure signals from the catheter and operative to convert the blood pressure signals into electric signals;

a housing;

securement means on the housing operative to secure the housing to a patient's body at a location proximate the location of the catheter insertion;

a monitoring device mounted in the housing and including electric circuitry arranged to receive the electrical signals from the transducer and operative to generate at least one display indicative of a condition of the patient's blood pressure;

a battery positioned within the housing and operative to power the electric circuitry; and a switch associated with the housing for connecting the battery into the electric circuitry to power the circuitry;

the kit further including a conduit having a first end in fluid communication with the catheter, a second end, and an intermediate operative portion juxtaposed to the transducer and operative to conduct blood pressure signals from the catheter to the transducer;

the kit further including means for flushing the conduit;

the conduit flushing means comprising a pressurized reservoir mounted on the housing, containing a flushing solution, and having an outlet communicating with the conduit at a location between the second conduit end and the transducer.

16. A miniature blood pressure monitoring kit comprising:

a housing;

a catheter adapted to be inserted into a blood vessel of a patient;

a conduit formed of a tubular material and including a first end in fluid communication with the catheter, a flexible connector portion extending between the first conduit end and the housing, and an operative portion carried by the housing and communicating in fluid communication with the connector portion;

a transducer carried by the housing and positioned in operative association with the operative portion of the conduit and operative to receive blood pressure signals from the operative portion of the conduit and convert the blood pressure signals into electrical signals;

a monitoring device mounted in the housing and including electric circuitry arranged to receive the electrical signals from the transducer and operative to generate at least one display indicative of a condition of the patient's blood pressure;

a battery positioned within the housing and operative to power the electric circuitry;

a switch associated with the housing for connecting the battery into the electric circuitry to power the circuitry; and securement means on the housing operative to secure the housing to a patient's body at a location proximate the location of the catheter insertion;

the conduit including a second end position exteriorly of the housing and the kit further including a stopcock secured to the second end of the conduit to enable flushing of the conduit and catheter through the second end of the conduit, the conduit flushing means comprising a pressurized reservoir mounted on the housing and containing a flushing solution.

* * * * *